United States Patent [19]
Barnett et al.

[11] Patent Number: 5,486,614
[45] Date of Patent: Jan. 23, 1996

[54] INTERMEDIATES FOR PREPARING ANTIFOLATE COMPOUNDS

[75] Inventors: Charles J. Barnett, Indianapolis; Thomas M. Wilson, Speedway, both of Ind.

[73] Assignee: Eli Lilly and Company, Indianapolis, Ind.

[21] Appl. No.: 453,529

[22] Filed: May 30, 1995

Related U.S. Application Data

[60] Division of Ser. No. 96,099, Jul. 23, 1993, which is a continuation-in-part of Ser. No. 961,572, Oct. 15, 1992, abandoned.

[51] Int. Cl.$^6$ .................. C07D 211/78; C07D 405/06; C07D 409/06
[52] U.S. Cl. ................. 546/207; 546/212; 546/214; 546/221; 544/279
[58] Field of Search ................. 546/207, 212, 546/214, 221

[56] References Cited

U.S. PATENT DOCUMENTS

| | | | |
|---|---|---|---|
| 4,501,890 | 2/1985 | Nichols et al. | 514/267 |
| 4,814,335 | 3/1989 | Kim | 514/257 |
| 4,946,846 | 8/1990 | Nomura et al. | 514/258 |
| 5,008,391 | 4/1991 | Barnett et al. | 546/243 |

OTHER PUBLICATIONS

Barnett, et al., *Tetrahedron Letters*, 30:6291–6294 (1989).
Miwa, et al., *J. Med. Chem.*, 34:555–560 (1991).
Larsen, C., et al., *Liebigs Ann. Chem.*, 819–823 (1989).
*The Chemistry of Functional Groups*, 2, part 2:1295–1296 (Patai, S., Ed., 1989).
Szcycinski, B., *Chem. Abs.*, 90:168638w (1978).
Snider, T. E., et al., *Org. Prep. and Procedures Int.*, 4(5):237–245 (1972).
DeGraw, J., et al., *Canadian J. Chem.*, 41:3137–3139 (1963).

Primary Examiner—Philip I. Datlow
Attorney, Agent, or Firm—Margaret M. Brumm; Steven A. Fontana; David E. Boone

[57] ABSTRACT

This invention relates to intermediates, and processes thereto, for the preparation of tetrahydropyrido[2,3-d]pyrimidines which are useful for the treatment of susceptable neoplasms. The intermediates have the following formula II;

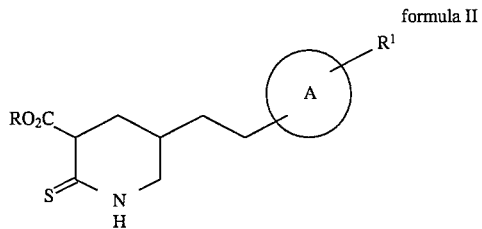

wherein the R, $R^1$ and A groups are as defined in the specification.

10 Claims, No Drawings

INTERMEDIATES FOR PREPARING ANTIFOLATE COMPOUNDS

This application is a division of application Ser. No. 08/096,099, filed Jul. 23, 1993 which is a continuation-in-part of application Ser. No. 07/961,572 filed Oct. 15, 1992, now abandoned.

BACKGROUND OF THE INVENTION

This invention relates to the fields of pharmaceutical and organic chemistry, and provides novel intermediates which are useful in the synthesis of tetrahydropyrido[2,3-d]pyrimidine (tetrahydrofolic acid) antimetabolites of the antifolate type. This invention also relates to processes for the preparation of such intermediates.

Substituted pyrido[2,3-d]pyrimidine-based antifolates have been used for a number of years as chemotherapeutic agents in the treatment of cancer. One such drug, methotrexate, is now one of the most widely used anticancer drugs; and many other compounds in the folic acid family have been synthesized, tested and discussed in the chemical and medical literature. The compounds have various activities at the enzymatic level; they inhibit such enzymes as dihydrofolate reductase, folate polyglutamate synthetase, glycinamide ribonucleotide formyltransferase and thymidylate synthase.

More particularly, a tetrahydrofolic acid antitumor agent, 5,10-dideaza-5,6,7,8-tetrahydrofolic acid (DDATHF/lometrexol), inhibits glycinamide ribonucleotide transformylase (GARFT), an enzyme required in the initial stage of de novo purine biosynthesis. See, U.S. Pat. No. 4,685,653; *J, Med, Chem.*, 28:914 (1985). However, the process for preparing lometrexol, and analogs thereof, has not been optimized.

The present invention provides a novel intermediate, and processes thereto, which help to optimize the process for preparing tetrahydrofolic acid derivatives.

SUMMARY OF THE INVENTION

The present invention relates to compounds having the formula

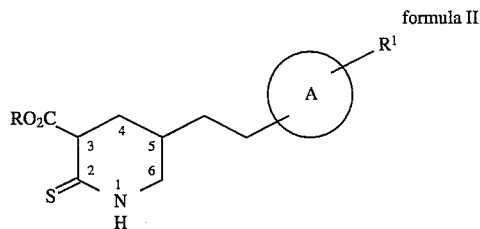

formula II wherein
R is $C_1$–$C_4$ alkyl or phenyl which may be substituted;
$R^1$ is bromo, iodo or $COOR^2$;
$R^2$ is H, $C_1$–$C_4$ alkyl, phenyl which may be substituted or benzyl; and
Ⓐ is an aryl group which may be substituted; or a salt thereof.

This invention also relates to a process for preparing a tetrahydropyrido [2,3-d]pyrimidine of the formula

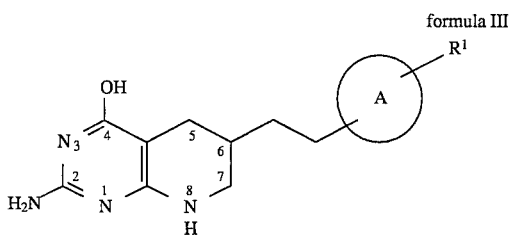

formula III wherein
$R^1$ and Ⓐ are as defined above, which comprises
(a) reacting a compound of formula I

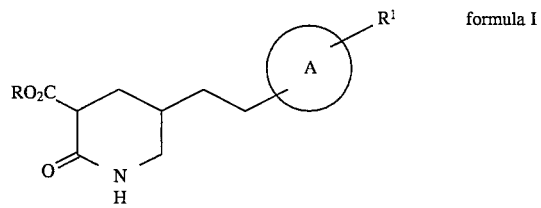

formula I wherein
R is $C_1$–$C_4$ alkyl or phenyl which may be substituted; and
$R^1$ is bromo, iodo or $COOR^2$;
$R^2$ is H, $C_1$–$C_4$ alkyl, phenyl which may be substituted or benzyl; and
Ⓐ is an aryl group which may be substituted; or a salt thereof, with a sulfurization agent;
(b) cyclizing the reaction product from step (a) with guanidine; and
(c) optionally salifying the reaction product from step (b).

A further aspect of this invention includes only steps (b) and (c) of the process described above.

Furthermore, this invention relates to another process for preparing a compound of formula III

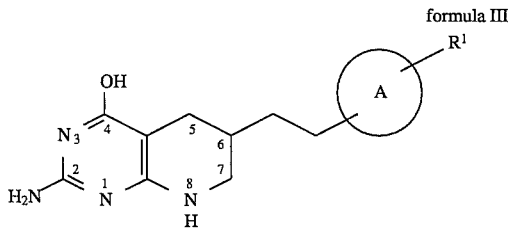

formula III wherein
$R^1$ is $COOR^2$;
$R^2$ is H; and
Ⓐ is an aryl group which may be substituted; or a salt thereof, which comprises
(a) reacting a compound of formula I

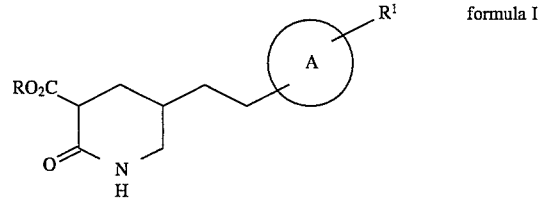

formula I wherein
R is $C_1$–$C_4$ alkyl or phenyl which may be substituted;
$R^1$ is $COOR^2$;
$R^2$ is t-butyl; and
Ⓐ is an aryl group which may be substituted; or a salt thereof, with a sulfurization agent;

(b) treating the reaction product from step (a) with a strong acid;
(c) cyclizing the reaction product from step (b) with guanidine; and
(d) optionally salifying the reaction product from step (c).

Another aspect of this invention relates only to steps (c) and (d) of the process described in the immediately preceding paragraph.

DETAILED DESCRIPTION OF THE INVENTION

The present invention pertains to novel intermediate compounds which are valuable for the preparation of tetrahydropyrido[2,3-d]pyrimidine derivatives and processes thereto.

Tetrahydropyrido[2,3-d]pyrimidines, particularly 5,10-dideaza-5,6,7,8-tetrahydrofolic acid derivatives such as DDATHF (lometrexol, formula IV below), have an inhibitory effect on one or more enzymes which utilize folic acid and, in particular, metabolic derivatives of folic acid as a substrate. Neoplasms in animals which depend upon such enzymes for growth are susceptible to treatment when an effective amount of this type of active compound is administered to such an animal. Thus, the intermediate compounds of this invention, and processes thereto, are useful for the preparation of tetrahydropyrido[2,3-d]pyrimidines which may be utilized for the treatment of susceptible neoplasms in animals, particularly humans.

The numbering system used for the pyridopyrimidine moiety of the compound of formula IV is shown below. The same numbering system is used for compounds of formula III.

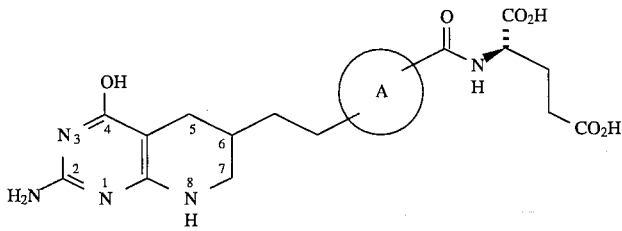

As shown above in formula IV, the configuration of the L-glutamic acid residue is shown unambiguously. The glutamic acid residue for all compounds disclosed herein is the L-configuration. In addition, there exists an asymmetric center at the 5-position of formula I and II compounds and at the 6-position of formula III and IV compounds. If desired, the individual enantiomers (formula I–III compounds) or diastereomers (formula IV compounds) may be separated by standard methods of resolution. Each of the enantiomers/diastereomers which can be separated by such a method are included in this invention.

Furthermore, there exists an asymmetric center at the 3-position of compounds of formulae I and II. However, this center is eliminated upon cyclization with guanidine, and the configuration does not influence the direction or efficiency of the process.

Compounds of formulae III and IV exist in tautomeric equilibrium with the corresponding 4(3H)-oxo compounds. For illustrative purposes, the equilibrium for the pyridopyrimidine system are shown below:

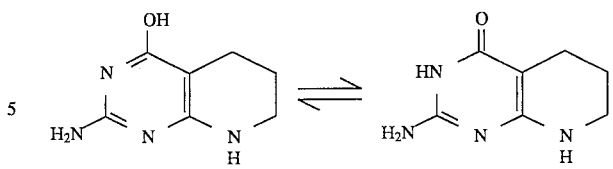

For convenience, the 4-hydroxy form is depicted for formulae III and IV, and the nomenclature is used throughout this specification. However, it is understood that such depictions include the corresponding tautomeric 4(3H)-oxo forms.

Furthermore, compounds of formula II (including formulae IIa and IIb, see Equation 2, infra) exist in tautomeric equilibrium with the 2-mercapto compound. For convenience, the 2-thiocarbonyl form is depicted for formula II, and the corresponding nomenclature is used throughout this specification. However, it is understood that such depictions include the corresponding tautomeric 2-mercapto forms.

The term "$C_1$–$C_4$ alkyl" refers to the straight or branched aliphatic chains of 1–4 carbon atoms, including methyl, ethyl, propyl, isopropyl, n-butyl, isobutyl, secbutyl and tert-butyl (t-butyl).

The term "phenyl which may be substituted" denotes an unsubstituted or substituted phenyl residue, optionally having one or two substituents selected from halo, nitro, $C_1$–$C_4$ alkyl and $C_1$–$C_4$ alkoxy.

The term "$C_1$–$C_4$ alkoxy" represents a $C_1$–$C_4$ alkyl group attached through an oxygen bridge, such as, for example, methoxy, ethoxy, n-propoxy, isopropoxy and the like.

The term "an aryl group which may be substituted" as used in describing the ring structure identified in Ⓐ in formulae I, II, III, and IV refers to 5- to 6-membered aromatic residues, including heterocyclic groups containing up to three heteroatoms (e.g., N, O, and S) therein, such as, for example, phenyl, thienyl, pyridyl, furyl, and the like. Of these aromatic residues, 1,4-phenylene, 2,5-thiophene, and 2,5-furan are preferred. Such aryl groups optionally may be substituted, in addition to the $R^1$ group, with one or two substituent groups selected from halo, hydroxy, C1–C4 alkyl, and C1–C4 alkoxy.

The carboxyl protecting groups of R and $R^2$, when $R^2$ is not H, denote groups which generally are not found in final therapeutic compounds, but which are intentionally introduced during a portion of the synthetic process to protect a group which otherwise might react in the course of chemical manipulations, and is then removed at a later stage of the synthesis. Since compounds bearing such protecting groups are of importance primarily as chemical intermediates (although some derivatives also exhibit biological activity), their precise structure is not critical. Numerous reactions for the formation and removal of such protecting groups are described in a number of standard works including, for example, *Protective Groups in Organic Chemistry*, Plenum Press, (London and New York, 1973); Greene, Th. W.,

*Protective Groups in Organic Synthesis,* Wiley, (New York, 1981); and *The Peptides,* Vol. I, Schroöder and Lubke, Academic Press, (London and New York, 1965).

Respresentative R carboxyl protecting groups include $C_1$–$C_4$ alkyl and phenyl which may be substituted. Representative $R^2$ groups, when $R^2$ is not H, include $C_1$–$C_4$ alkyl, phenyl which may be substituted or benzyl. These groups are selectively removable under sufficiently mild conditions so as not to disrupt the desired structure of the molecule.

When $R^2$ is not H, it is preferred that carboxyl protecting groups R and $R^2$ are not the same group. Thus, preferred R groups are $C_1$–$C_4$ alkyl, especially ethyl; when R is ethyl, the preferred $R^2$ group is t-butyl.

The process and compounds of this invention also include salts of the compounds defined by the above formulas. A particular compound of this invention can possess a sufficiently acidic, a sufficiently basic, or both functional groups, and accordingly react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromo-phenyl-sulfonic acid, carbonic acid, succinic acid, citric acid, benzoic acid, acetic acid, and the like. Examples of such salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate. The potassium and sodium salt forms are particularly preferred.

Of course, when the intermediates of this invention are converted to final, pharmaceutically active compounds, those compounds may also be in the form of a salt, but the salt must be of the pharmaceutically acceptable nature.

Processes for preparing acid addition, base addition, and pharmaceutically acceptable salts (salification) are well known in the art.

Preferred starting material for preparing compounds of the present invention include 2-oxo-3-($C_1$–$C_4$ alkyl)carboxy-5-[(4-bromo- or 4-iodophenyl)ethyl] piperidine or 2-oxo-3-($C_1$–$C_4$ alkyl)carboxy-5-[(4-protected carboxyphenyl)ethyl]piperidine (both of formula I below), depending on the desired $R^1$ substituent. Other preferred starting material include 2-oxo-3-($C_1$–$C_4$ alkyl)carboxy-5-[ (5-bromo- or 5-iodothienyl or -furanyl)ethyl]piperidine or 2-oxo-3-($C_1$–$C_4$ alkyl)carboxy-5-[(5-protected carboxythienyl or carboxyfuranyl)ethyl]piperidine (also of formula I below). The desirability and use of different $R^1$ substituents, bromo, iodo, carboxyl or protected carboxyl, are further discussed following Equation 2.

Preparation of these starting materials are generally known in the organic chemical art (see, e.g. Barnett, et al., *Tetrahedron Letters,* 30:6291–6294 (1989) and Barnett, et al., U.S. Pat. No. 5,008,391, respectively).

Regarding formula I compounds wherein $R^1$ is bromo or iodo, one will note that the desired halogen is present on this starting material prior to the first step of the process for preparing compounds of formulae III and IV, and can remain as such prior to coupling of compounds of formula III with L-glutamic acid to produce therapeutically active tetrahydrofolic acid derivatives.

Likewise, the protected aryl carboxyl group of formula I compounds is also present at that position prior to the first step of the process. Preferred $R^2$ carboxyl protecting groups include $C_1$–$C_4$ alkyl, phenyl which may be substituted or benzyl. Of these, t-butyl is especially preferred. As previously mentioned, compounds of formula I possess an asymmetric center at the 5-position of the piperidine ring, of which the diastereomers thereof may be separated and purified. Under the reactive conditions of the processes of the present invention, a selected diastereomer will remain as such throughout each step. Thus, if the 6R isomer of formula III or formula IV is desired, the 5R isomer of a formula I compound should be selected as the starting material.

In one process, a formula I compound is sulfurized to form a thiopiperidone (formula II), which is then cyclized to form a compound of formula III. This process is novel and is depicted in Equation 1.

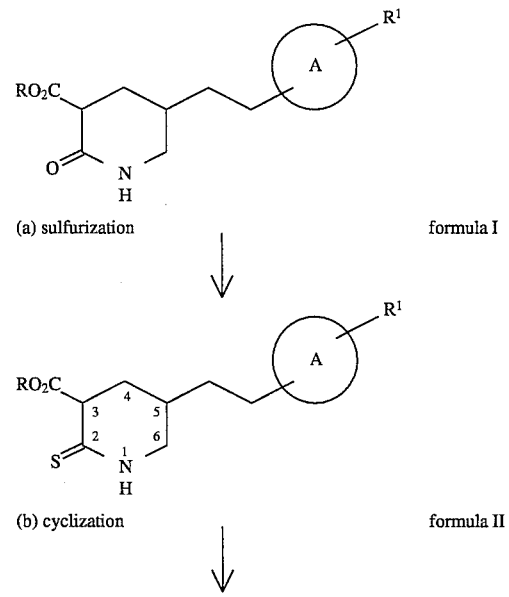

Equation I (a) sulfurization    formula I (b) cyclization    formula II

-continued
Equation I

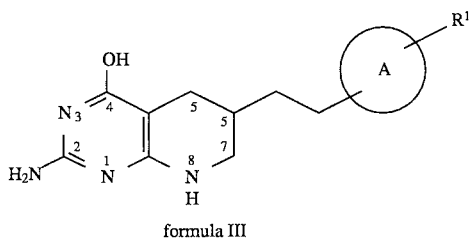

formula III wherein R is $C_1$–$C_4$ alkyl or phenyl which may be substituted; $R^1$ is bromo, iodo or $COOR^2$; $R^2$ is H, $C_1$–$C_4$ alkyl, phenyl which may be substituted or benzyl; Ⓐ is an aryl group which may be substituted; or a salt thereof. As mentioned above, formula III compounds optionally may be salified via known procedures.

The first step of Equation 1 involves the sulfurization of a formula I compound. Although a number of sulfurization agents, such as Lawesson's reagent (see, e.g., *Organic Synthesis Highlights,* Mulzer, et al., (Weinhein and New York, 1991), may be used in this step, sulfurization is preferably accomplished using phosphorous pentasulfide.

The amount of sulfurization agent employed is suitably an amount sufficient to replace the 2-carbonyl moiety on the piperidone ring by thiocarbonyl. Generally, about one equivalent of sulfurization agent per equivalent of piperidone is employed. Preferably, an excess of sulfurization agent is used.

The first step shown in Equation 1 is accomplished in the presence of a suitable inert, or substantially inert solvent, or mixture of solvents. A solvent such as tetrahydrofuran is preferred.

The temperature employed in this step should be sufficient to effect completion of the sulfurization reaction. Typically, a temperature in the range from about 50° C. to about 70° C. is sufficient, whereas a temperature of about 60° C. is preferred.

The length of time for this sulfurization step to occur can vary. The reaction generally requires from about a few minutes to about a few hours. The optimal reaction time can be determined by monitoring the progress of the reaction by conventional chromatographic techniques such as thin layer chromatography, high performance liquid chromatography or column chromatography.

In the second step of Equation 1, the thiopiperidone of formula II is reacted with guanidine, in an appropriate solvent, and forms a compound of formula III. For this cyclization to occur, guanidine may be supplied as a salt, but it must first be converted to the free base via neutralization with a base. Thus, it is preferred to employ guanidine free base in this step of the reaction.

Appropriate solvents include any solvent, or mixture of solvents, which will remain inert, or substantially inert, under reaction conditions. Typically, appropriate solvents include $C_1$–$C_4$ aliphatic alcohols such as methanol, ethanol, 1-propanol, 2-propanol, 1-butanol, 2-butanol and 2 methyl-2-propanol. Of these, ethanol is preferred.

Suitable amounts of guanidine are those which are sufficient to react with all of a formula II compound from step (a) of the reaction shown in Equation 1. Generally, from about one equivalent to an excess of guanidine per equivalent of a formula II compound is employed. Preferably, an excess of guanidine is used.

Typically, this step proceeds in short periods of time at elevated temperatures, but the length of time will vary with the reaction conditions employed. This cyclization reaction requires about 10 to about 30 minutes to proceed when run at the preferred temperature of about 90° C. However, this reaction may be run in a temperature range from about 70° C. to about 100° C.

Each step of the novel process depicted in Equation 1 may be individually run wherein each reaction product is isolated and purified. Not only is the entire process shown in Equation 1 novel, but the second step, the cyclization of a formula II thiopiperidone with guanidine, [step (b)], independently is a novel process. It is preferred that the steps shown in Equation 1 are combined into a one-pot process comprising reacting a compound of formula I with a sulfurization agent and cyclizing the reaction product from the immediately preceding step (a formula II compound) by reacting that reaction product with guanidine. The compounds of formula II also are novel and are useful as intermediates for the preparation of tetrahydrofolic acid derivatives.

Alternatively, when the processes of this invention are used to prepare an intermediate of formula III wherein $R^1$ is $COOR^2$ and $R^2$ is H, it is preferred to use the novel process depicted in Equation 2. The preferred starting material is a compound of formula I wherein $R^1$ is $COOR^2$ and $R^2$ is t-butyl. However, compared to the process shown in Equation 1, an additional step is preferred.

Equation 2

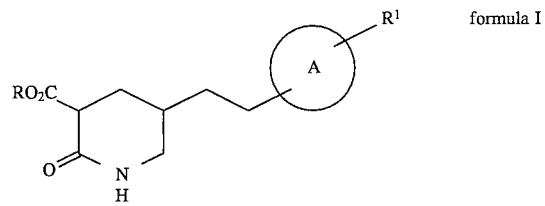

formula I wherein R is $C_1$–$C_4$ alkyl or phenyl which may be substituted, $R^1$ is $COOR^2$, $R^2$ is t-butyl, and Ⓐ is an aryl group which may be substituted;

(a) sulfurization

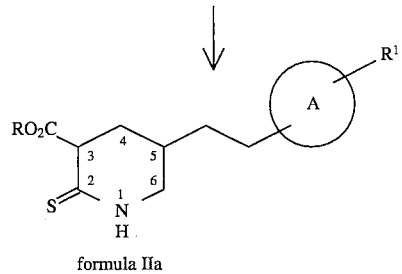

formula IIa wherein R, $R^1$, and Ⓐ are as defined above;

(b) conversion to acid

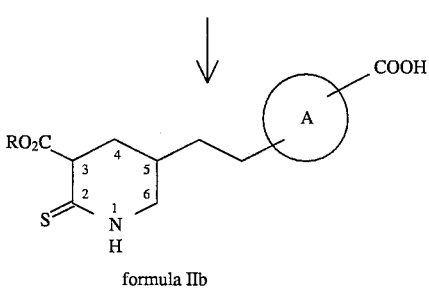

formula IIb wherein R and Ⓐ are as defined above, or a salt thereof;

(c) cyclization

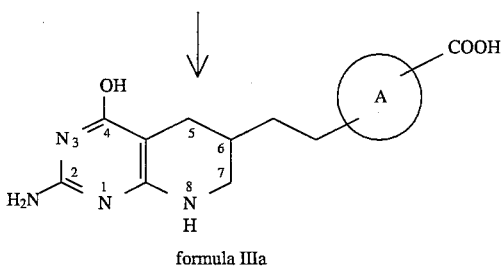

formula IIIa wherein Ⓐ is an aryl group which may be substituted, or a salt thereof. The reaction product from step (c) also may be salified as previously discussed.

Steps (a), (c), and (d) of the process shown in Equation 2, including all general and preferred reagents and reaction conditions, are the same as steps (a), (b) and (c) respectively, described above for Equation 1. In Equation 2, however, there is the preferred additional step of converting the thiopiperidone of formula IIa to its acid form [step (b)], which provides compounds of formula IIb.

In essence, it is not necessary to convert the protected thiopiperidone of formula IIa to the acid form prior to cyclization with guanidine. However, it is best to unmask the carboxyl group prior to cyclization because the $R^2$ protected carboxyl group could react with guanidine to produce undesirable results.

Thus, the selection of t-butyl as the $R^2$ substituent, as shown in Equation 2, allows for the conversion of this protecting group to the acid form via an acid catalyst [step (b)]. Suitable acid catalysts can be any organic or inorganic compound which will facilitate removal of the t-butyl protecting group from the benzoic acid moiety of a formula IIa compound. Such acid catalysts are well known in the art. See, e.g., *Protective Groups in Organic Chemistry*, J. G. W. McOmie, Ed., Plenum Press (New York, 1973); and T. W. Greene, *Protective Groups in Organic Synthesis*, John Wiley and Sons (New York, 1981). However, the preferred acid catalyst is trifluoroacetic acid, especially when used in substantial excess per equivalent of substrate present.

Generally, this step of the reaction takes place nearly instantaneously, but the length of time required depends upon the choice of acid catalyst and its effectiveness in the process.

Although other $C_1$-$C_4$ alkyl substituents could be converted to form the acid, the presence of t-butyl as the $R^2$ substituent permits this conversion without hydrolysis or displacement, leaving the R substituent undisturbed. By converting the $R^2$ substituent while leaving the R substituent as originally selected, cyclization at the desired location is favored and the potential for guanidine to react with the $R^2$ protected carboxyl group is eliminated.

Each step of the novel process depicted in Equation 2 may be individually run wherein each reaction product is isolated and purified. It is preferred, however, that the steps shown in Equation 2 are combined in a one-pot process comprising reacting a compound of formula I with a sulfurization agent, treating the reaction product from the previous step with a strong acid, and cyclizing the reaction product from the step (b) with guanidine. In addition, the cyclization of a formula IIb compound with guanidine is independently a novel process.

The final reaction product of both Equation 1 and Equation 2, a formula III compound, is easily converted to a therapeutically active tetrahydrofolic acid derivative by conventional methods.

Generally, the $R^1$ substituent on formula III compounds, when $R^1$ is bromo or iodo, is replaced with cyano by reaction with a cyano salt such as copper cyanide in the presence of N-methylpyrrolidine. The nitrile group is then hydrolyzed to obtain a formula III compound with a carboxyl or protected carboxyl group (see, e.g., U.S. Pat. No. 5,008,391).

A formula III compound is then coupled with a protected L-glutamic acid derivative in the manner described in U.S. Pat. No. 4,684,653, using conventional condensation techniques for forming peptide bonds. The protected L-glutamic acid derivative is then subjected to hydrolysis to remove the remaining carboxyl protecting groups.

The following examples further illustrate the level intermediate compounds, and processes thereto, according to the present invention. The examples are not intended to be limiting to the scope of the invention in any respect, and should not be so construed.

In the following examples, the terms melting point, nuclear magnetic resonance spectra, electron impact mass spectra, field desorption mass spectra, infrared spectra, ultraviolet spectra, and elemental analysis, are abbreviated mp, NMR, MS(EI), MS(FD), IR, UV, and Anal., respectively. In general, the adsorption maxima listed are only those of interest and not necessarily all of the maxima observed.

The NMR spectra were obtained on a General Electric QE-300 300 MHz instrument. The chemical shifts are expressed in δ values (parts per million downfield from tetramethylsilane). The field desorption mass spectra were taken on a Varian-MAT 731 Spectrometer using carbon dendrite emitters. Electron impact mass spectra were obtained on a CEC 21-110 instrument from Consolidated Electrodynamics Corporation. Infrared spectra were obtained on a Perkin-Elmer 281 instrument. Ultraviolet spectra were obtained on Cary 118 instrument. Melting points are uncorrected.

EXAMPLE 1

(3RS,5R)-2-Thioxo-3-(ethylcarboxy-5-[2-(4-bromophenyl)ethyl]piperidine

A mixture of 1.12 g (3.16 mmol) of (3RS, 5R)-2-oxo-3-ethylcarboxy-5-[2-(4-bromophenyl)ethyl]piperidine and 0.77 g (1.74 mmol) of phosphorus pentasulfide in 20 mL of tetrahydrofuran was heated at 60° C. until complete conversion was obtained (about 3 hours). The mixture was evaporated to a residue which was purified by chromatography on silica gel. The product was eluted with ethyl acetate-hexane 1:1, affording 0.729 g (61%) of (3RS, 5R)-2-thioxo-3-ethylcarboxy-5-[2-(4-bromophenyl)ethyl] piperidine (mixture of C-3 epimers)), mp 105°–115° C., $^1$H NMR (300 MHz, CDCl$_3$) δ 9.47 (s, 1H), 7.41 (d, J=8.7 Hz,); 7.39 (d, J=8.2 Hz,), total 2H, 7.02 (d, J=8.7 Hz, 2H), 4.20 (m, 2H), 3.94 (m); 3.69 (m), total 1H, 3.45 (m, 1H), 2.99 (m, 1H), 2.60 (m, 2H), 2.13 (m, 2H), 1.5–1.87 (m, 3H), 1.31 (t, J=7.1 Hz); 1.26 (t, J=7.1 Hz), total 3H; IR (CHCl$_3$) 2983, 1731, 1540, 1489, 1373, 1073, 1012 cm$^{-1}$; MS (FD) m/z 371 (100), 369 (75); UV (EtOH) 219.8 nm (ε 13 174), 281.4 (13 557); Anal. Calcd for C$_{16}$H$_{20}$BrNO$_2$S: C, 51.90; H, 5.44; N, 3.78. Found: C, 51.61; H, 5.38; N, 3.88.

EXAMPLE 2

R-(−)-2-Amino-4-hydroxy-6-[(4-bromophenyl)ethyl]-5,6,7,8-tetrahydropyrido[2,3-d]pyrimidine A suspension of 740 mg (7.77 mmol) of guanidine hydrochloride in 5 mL of ethanol was neutralized by addition of 950 mg (7.77 mmol) of potassium tert-butoxide. The precipitated potassium chloride was filtered with filter aid and washed with an additional 5 mL of ethanol. A solution of 720 mg (1.94 mmol) of (3RS, 5R)-2-thioxo-3-ethylcarboxy-5-[2-(4-bromophenyl)ethyl]piperidine in 5 mL ethanol was added to the filtrate and this solution was reduced to a volume of 2–3 mL under vacuum. The solution was heated in an oil bath (T=90° C.) under a stream of nitrogen for 2 h. After cooling to ambient temperature, the mixture was subjected to further vacuum evaporation. The resulting solid was suspended in water, sonicated to form a uniform suspension, and neutralized to pH 7 by addition of 1N aq. HCl. The resulting suspension was heated to about 90° C. for 15 min, then cooled to ambient temp. and filtered. The product was dried in vacuo (10 torr), affording 544 mg (80%) of (R)-(−)-2-amino-4-hydroxy- 6-[2-(4-bromophenyl)ethyl]-5,6,7,8-tetrahydropyrido[2,3-d] pyrimidine mp 275°–283° C., [α]$_{589}$ −30.9° (c 1, DMF), $^1$H NMR (DMSO-d$_6$) δ9.70 (bs, 1H), 7.40 (d, J=8.3 Hz, 2H), 7.12 (d, J=8.3 Hz, 2H), 6.23 (d, J=8.3 Hz, 2H), 5.96 (s, 2H), 3.15 (bd, J=11 Hz, 1H), 2.45 (m, 2H), 1.78 (dd, J=8.6, 15.1, 1H), 1.50 (m, 3H); IR (KBr) 3400, 3343, 1678, 1642 cm$^{-1}$; MS (EI), m/z 350 (78), 348 (72), 166 (100), 165 (95), 164 (31), 151 (68), 139 (19). The NMR spectrum was identical with that of a sample of (S)-(+)-3 obtained as described in U.S. Pat. No. 5,008,391.

EXAMPLE 3

4-(2-[2-thioxo-3-ethylcarboxypiperidin-5-yl] ethyl)benzoic acid, 2,2-dimethylethyl ester A mixture of 3.75 g (10 mmol) of 4-(2-[2-oxo-3-ethylcarboxypiperidin-5-yl]ethyl)benzoic acid, 2,2-dimethylethyl ester and 2.44 g (5.5 mmol) of phosphorus pentasulfide in 70 mL of tetrahydrofuran is heated at 60° C. until complete conversion is obtained. The mixture is evaporated to a residue which is purified by chromatography on silica gel, providing 4-(2-[2-thioxo-3-ethylcarboxypiperidin-5-yl]ethyl)benzoic acid, 2,2-dimethylethyl ester.

EXAMPLE 4

4-(2-[2-amino-4(1H)-oxo-5,6,7,8-tetrahydropyrido[2,3-d]pyrimidin-6-yl]ethyl)benzoic acid, 2,2-dimethylethyl ester A suspension of 764 mg (8.0 mmol) of guanidine hydrochloride in 5 mL of ethanol is neutralized by addition of 976 mg (8.7 mmol) of potassium tert-butoxide. The precipitated potassium chloride is filtered with filter aid and washed with an additional 5 mL of ethanol. A solution of 783 mg (2.0 mmol) of 4-(2-[2-thioxo-3-ethylcarboxypiperidin-5-yl]ethyl)benzoic acid, 2,2-dimethylethyl ester in 5 mL ethanol is added to the filtrate and this solution is reduced to a volume of 2–3 mL under vacuum. The solution is heated in an oil bath to about 90° C. under a stream of nitrogen for about 2 h. After cooling to ambient temperature, the mixture is subjected to further vacuum evaporation. The resulting solid is suspended in water, sonicated, if necessary, to form a uniform suspension, and neutralized to pH 7 by addition of 1N aq. HCl. The resulting suspension is filtered and dried, affording 4-(2-[2-amino-4(1H)-oxo- 5,6,7,8-tetrahydropyrido[2,3-d]pyrimidin-6-yl]ethyl)benzoic acid, 2,2-dimethylethyl ester.

We claim:

1. A compound of formula II

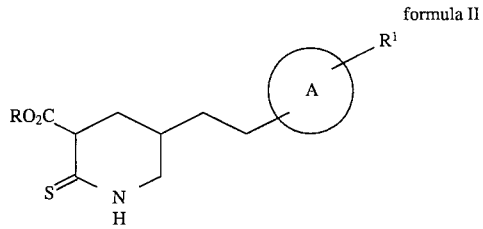

formula II wherein

R is C$_1$–C$_4$ alkyl or phenyl which may be substituted;

R$^1$ is bromo, iodo or COOR$^2$;

R$^2$ is H, C$_1$–C$_4$ alkyl, phenyl which may be substituted or benzyl; and

Ⓐ is an aryl group which may be substituted; or a salt thereof.

2. A compound according to claim 1 wherein R is ethyl.

3. A compound according to claim 1 wherein R$^1$ is bromo.

4. A compound according to claim 1 wherein R$^1$ is COOR$^2$, and R$^2$ is H or t-butyl.

5. A compound according to claim 4 wherein Ⓐ is 1,4-phenylene.

6. A compound according to claim 4 wherein Ⓐ is 2,5-thiophene.

7. A compound according to claim 4 wherein Ⓐ is 2,5-furan.

8. A compound according to claim 3 wherein Ⓐ is 1,4-phenylene.

9. A compound according to claim 3 wherein Ⓐ is 2,5-thiophene.

10. A compound according to claim 3 wherein Ⓐ is 2,5-furan.

* * * * *